(12) United States Patent
Lee et al.

(10) Patent No.: US 8,399,033 B2
(45) Date of Patent: Mar. 19, 2013

(54) **ANTI-BACTERIAL COMPOSITION COMPRISING EXTRACT FROM BARKS OF *ALNUS PENDULA* MATSUM**

(75) Inventors: Min Won Lee, Seoul (KR); Sun Eun Choi, Seoul (KR); Manh Heun Kim, Seoul (KR); Dong Yeul Kwon, Daejeon (KR); Jang-Gi Choi, Jinju-Si (KR)

(73) Assignee: Chung-Ang University Industry Academic Cooperation Foundation, Seoul (KR)

( * ) Notice: Subject to any disclaimer, the term of this patent is extended or adjusted under 35 U.S.C. 154(b) by 40 days.

(21) Appl. No.: 12/659,518

(22) Filed: Mar. 11, 2010

(65) Prior Publication Data

US 2011/0033566 A1 Feb. 10, 2011

(30) Foreign Application Priority Data

Aug. 10, 2009 (KR) ........................ 10-2009-0073299

(51) Int. Cl.
*A61K 36/00* (2006.01)

(52) U.S. Cl. ....................................... 424/769

(58) Field of Classification Search ........................ None
See application file for complete search history.

(56) References Cited

U.S. PATENT DOCUMENTS

2005/0215635 A1 9/2005 Rafi et al.

OTHER PUBLICATIONS

Venkateswarlu et al. "Synthesis of gingerone=A and hirsutenone". Indian Journal of Chemistry, vol. 40B (Jun. 2001) 495-497.*
Dalhoff, A. "Pharmacodynamics of fluoroquinolones". Journal of Antimicrobial Chemotherapy, vol. 43, Suppl. B (1999) 51-59.*
Wang, Yu, et al. "Study on the antibiotic activity of microcapsule curcumin against foodborne pathogens". International Journal of Food Microbiology. 2009. vol. 136, pp. 71-74. Elsevier B.V.

* cited by examiner

*Primary Examiner* — Amy L Clark
(74) *Attorney, Agent, or Firm* — Nath, Goldberg & Meyer; Tanya E. Harkins

(57) ABSTRACT

The present invention relates to a composition for treating a bacterial infection comprising an extract from a bark of *Alnus pendula*, or diarylheptanoid compound as an active ingredient. The extract from a bark of *Alnus pendula*, diarylheptanoid compound of the present composition has a remarkably excellent anti-bacterial activity against bacteria, specifically *Staphylococcus aureus*. Therefore, the extract and compound of the present invention may be utilized as an active ingredient of drug, cosmetics, functional food and animal feed for treating bacterial infection, in particular an infection of *S. aureus*.

1 Claim, 3 Drawing Sheets

ANTI-BACTERIAL COMPOSITION COMPRISING EXTRACT FROM BARKS OF *ALNUS PENDULA* MATSUM

BACKGROUND OF THE INVENTION

Field of the Invention

The present invention relates to compositions for treating a bacterial infection comprising an extract from a bark of *Alnus pendula* Matsum or a diarylheptanoid compound as an active ingredient.

BACKGROUND OF TECHNIQUE

The genus *Alnus* spp. belongs to Betulaceae family. Thirty species grows naturally in the Northern South America (1) and seventeen species in Korea (2). Various studies for extracts from genus *Alnus* have contributed to identification of many compounds including diarylheptanoid compounds such as yashabushiketol, dihydroyashabushiketol, alnustone, hirsutanonol, hirsutenone, oregonin, biarylheptanoid, 1,7-diarylheptane-3,5-dione and platyphylloside, and triterpenoid compounds such as tannin, ellagitannin and dammarane (3-55). It has been reported that phenolic components of diarylheptanoid compounds in the genus *Alnus* are related to antioxidation, several adult diseases, cancers, immune disorders, diarrhea or inhibition of NO (nitric oxide) production (56-62). In addition, it has been demonstrated in in vitro experiment that oregonin, one of phenolic components of diarylheptanoid compounds which is abundant in the genus *Alnus*, specifically influences dendritic cells as atopic dermatitis-inducible biomark (63), suggesting that it could be used to develop a therapeutic agent for atopic dermatitis.

On the other hand, atopic dermatitis could be developed by interactions between several factors including hereditary factors, environmental factors, immunological factors, and so on. Although there have been reported several examples such as hyperactivation of B cells assessed by increase of total IgE concentration in serum, or dysregulation of T cell systems caused by immune regulatory cytokines, the etiology or development mechanism of atopic dermatitis remains to be elucidated. The skin property of subjects suffering from atopic dermatitis is as follows: (a) dryness, (b) sensitivity to damage and (c) feasible infection of bacteria or antigen (64, 65). Dry skin leads to pruritus and subsequently induces serious itching. This generates not only loss of dermal layer but also release of various inflammation-mediated substances. Pruritus gets worse due to higher reactivity of free radicals produced by photo-aging and excessive stress (66, 67).

Even though there are mechanisms to repair proteins and genes damaged by intracellular radicals, imbalance between the production of free radicals and protection system, and massive production of free radicals cause the oxidation of biomolecules to block their original functions (68). As a result, lipid hyperoxidation and immune-related factors such as proteins, plasma membrane, DNA, enzyme and T cells are impaired, and inflammation substances shown in atopic dermatitis are released (69). These inflammation substances bring out bacterial infection and colonization in a feasible manner (70, 71), and bacteria colonization causes reduction of ceramide within horny layer to bring out a vicious cycle decreasing moisture regain (72, 73). The treatment is difficult because the secondary bacterial infection to skin induces symptoms of atopic dermatitis that is worse and prolonged. *Staphylococcus aureus*, most common one of causative strains, is occupied not more than 5% in colonization of normal humans, whereas is detected no less than 90% in skin of subjects suffering from atopic dermatitis (74). In addition, the number of *S. aureus* on the skin of subjects with atopic dermatitis is found in lesion portions 100-1,000-fold higher than in non-lesion portions, and the colonization of *S. aureus* is observed in non-lesion portions as well (75). As further evidence that *S. aureus* influences etiology of atopic dermatitis, there are reported that only the use of steroid drug partially plays a role in elimination of *S. aureus*, supposing the possibility that any immunological factor is related to the colonization of *S. aureus* (76).

The mechanism, in which the colonization of *S. aureus* is elevated on the skin of subjects with atopic dermatitis, has been known to be associated with several processes, for example including loss of skin barrier function, defect of natural anti-bacterial activity and eradication potential against bacteria, alkalization of skin acidity, deficiency of skin lipid, increased colonization due to skin dryness and enhanced attachment potential of *S. aureus*, and so forth (77). Meanwhile, the frequency of MRSA (Methicillin resistant *S. aureus*) was only about 1% in the 1970's, however rapidly increased by 10-50% in recent. In addition to *S. aureus*, other bacteria also were found even rarely, increasing the difficulty of treatment (78, 79).

Throughout this application, various publications and patents are referred and citations are provided in parentheses. The disclosures of these publications and patents in their entities are hereby incorporated by references into this application in order to fully describe this invention and the state of the art to which this invention pertains.

DETAILED DESCRIPTION OF THE INVENTION

The present inventors have made intensive studies to develop a substance having an anti-bacterial activity derived from natural materials. As results, we have discovered that an extract from a bark of *Alnus pendula* Matsum and a diarylheptanoid compound isolated from the extract exhibited an excellent anti-bacterial activity.

Accordingly, it is an object of this invention to provide a composition for treating a bacterial infection comprising an extract from a bark of *Alnus pendula*, or a diarylheptanoid compound as an active ingredient.

It is another object of the instant invention to provide a method of treating a bacterial infection in a subject in need of such treatment, which comprises administering to the subject an effective amount of an extract from a bark of *Alnus pendula*, or a diarylheptanoid compound.

Other objects and advantages of the present invention will become apparent from the following detailed description together with the appended claims and drawings.

In one aspect of this invention, there is provided a composition for treating a bacterial infection comprising an extract from a bark of *Alnus pendula*, or a compound represented by the following formula I or II as an active ingredient.

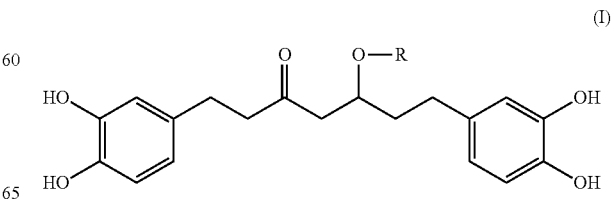

wherein R represents xylose in formula I.

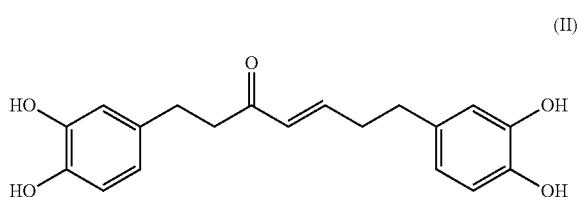
(II)

In another aspect of this invention, there is provided a method of treating a bacterial infection in a subject in need of such treatment, which comprises administering to the subject an effective amount of an extract from a bark of *Alnus pendula*, or a compound represented by the following formula I or II.

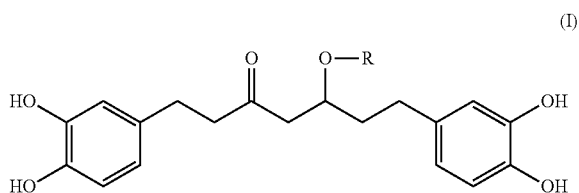
(I)

wherein R represents xylose in formula I.

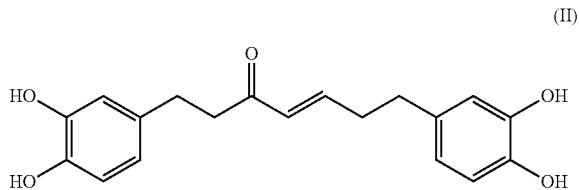 [SMILES: O=C(/C=C/CCc1ccc(O)c(O)c1)CCc1ccc(O)c(O)c1]
(II)

The present invention relates to a composition for treating a bacterial infection comprising an extract from a bark of *Alnus pendula* as an active ingredient.

The extract from a bark of *Alnus pendula* of the present composition could be obtained according to the conventional extraction method known to those skilled in the art, for example by employing conventional extraction solvents under conditions of typical temperature and pressure.

The solvent used in the instant invention may be an extraction solvent selected from the group consisting of water, anhydrous or hydrated lower alcohol containing 1 to 4 carbon atoms, acetone, ethylacetate, butylacetate and 1,3-butylene glycol.

According to a preferred embodiment of this invention, the extract of the present invention is a fraction obtained by further column chromatography purification of the extract prepared by using the extraction solvent. More preferably, the column chromatography purification is a gel-filtration and/or absorption column chromatography.

According to another preferred embodiment of the instant invention, the extract of the present invention has an anti-bacterial activity against *Staphylococcus aureus*. The extract of the present invention has an anti-bacterial activity against Methicillin Resistant *Staphylococcus aureus* as well as Methicillin Sensitive *Staphylococcus aureus*.

The present invention relates to a composition for treating a bacterial infection comprising a compound represented by the formula I or II as an active ingredient.

The present diarylheptanoid compound represented by formula I or II can be prepared by purifying the extract from the bark of *Alnus pendula*. The IUPAC name of the compound represented by formula I and formula II is [1,7-bis-(3,4-dihydroxyphenyl)-5-hydroxyheptane-3-on-5-O-β-D-xylopyranoside], and 1,7-bis-(3,4-dihydroxyphenyl)-4-heptene-3-one, respectively, which is well-known as the conventional name of "oregonin" and "hirsutenone" in the art. It is obvious to those skilled in the art that the compound represented by formula I or II of the present composition can be extracted from other plants of *Alnus* genus than *Alnus pendula* Matsum.

According to a preferred embodiment of this invention, the diarylheptanoid compound represented by formula I or II of the present composition exhibits an anti-bacterial activity against *Staphylococcus aureus*. The compound of the present invention has an anti-bacterial activity against Methicillin Resistant *Staphylococcus aureus* as well as Methicillin Sensitive *Staphylococcus aureus*.

According to another preferred embodiment of this invention, the composition of the present invention may be provided as a cosmetic composition.

The cosmetic compositions of this invention may be formulated in a wide variety of forms, for example, including a solution, a suspension, an emulsion, a paste, a gel, a cream, a lotion, a powder, a soap, a surfactant-containing cleanser, an oil, a powder foundation, an emulsion foundation, a wax foundation and a spray. Specifically, the cosmetic compositions of this invention may be formulated in the form of skin softner, nutrient liquid, nutrient cream, massage cream, essence, eye cream, cleansing cream, cleansing foam, cleansing water, pack, spray or powder.

Where the cosmetic composition is in the form of paste, cream or gel, it may comprise animal and vegetable fats, waxes, paraffins, starch, tragacanth, cellulose derivatives, polyethylene glycols, silicones, bentonites, silica, talc, zinc oxide or mixtures of these substances.

In the formulation of powder or spray, it may comprise lactose, talc, silica, aluminum hydroxide, calcium silicate, polyamide powder and mixtures of these substances. Spray may additionally comprise the customary propellants, for example, chlorofluorohydrocarbons, propane/butane or dimethyl ether.

The formulation of solution and emulsion may comprise solvent, solubilizer and emulsifier, for example water, ethanol, isopropanol, ethyl carbonate, ethyl acetate, benzyl alcohol, benzyl benzoate, propylene glycol, 1,3-butylglycol, oils, glycerol fatty esters, polyethylene glycol and fatty acid esters of sorbitan.

The formulation of suspension may comprise liquid diluents, for example water, ethanol or propylene glycol, suspending agents, for example ethoxylated isosteary alcohols, polyoxyethylene sorbitol esters and poly oxyethylene sorbitan esters, micocrystalline cellulose, aluminum metahydroxide, bentonite, agar and tragacanth or mixtures of these substances.

The formulation of cleansing compositions with surfactant may comprise aliphatic alcohol sulfate, aliphatic alcohol ether sulfate, sulfosucinnate monoester, isothinate, imidazolium derivatives, methyltaurate, sarcocinate, fatty acid amide ether sulfate, alkyl amido betain, aliphatic alcohol, fatty acid glyceride, fatty acid diethanolamide, vegetable oil, lanoline derivatives, ethoxylated glycerol fatty acid ester or mixtures of these ingredients.

Furthermore, the cosmetic compositions of this invention may contain auxiliaries as well as compounds as active ingredients and carriers. The non-limiting examples of auxiliaries include antioxidants, stabilizers, solubilizers, vitamins, colorants, odor improvers or mixtures of these substances.

The amount of the extract or the compound of formula I or II included in the present composition is not particularly limited, and can be preferably determined to accomplish sufficient anti-bacterial activities described hereinabove.

According to another preferred embodiment of this invention, the composition of the present invention may be provided as a functional food composition.

The functional food composition of the present invention may be formulated in a wide variety of forms, for example, including proteins, carbohydrates, fatty acids, nutrients and seasoning agents.

In the formulation of drinking agent, it may further include a flavoring agent or natural carbohydrates. For instance, natural carbohydrate may include monosaccharides (e.g., glucose, fructose, etc.); disaccharides (e.g., maltose, sucrose, etc.); oligosaccharides; polysaccharides (e.g., dextrin, cyclodextrin, etc.); and sugar alcohols (e.g., xylitol, sorbitol, erythritol, etc.). The formulation of flavoring agent may use natural flavoring agents (e.g., thaumatin, stevia extract, etc.) and synthetic flavoring agents (e.g., saccharine, aspartame, etc.).

According to still another preferred embodiment of this invention, the present composition may be provided as a feed additive composition for animals.

The extract from a bark of *Alnus pendula*, or the compound of formula I or II of the present invention may be utilized as an active ingredient in the feed additive composition for treating a bacterial infection in animals.

The amount of extract or the compound included in the feed additive composition of the present invention is not particularly restricted, and preferably includes a suitable amount to treat or improve a bacterial infectious disease in animals.

The composition of the present invention may further include one or more elements consisting of an organic acid such as citric acid, adipic acid, fumalic acid, lactic acid and malic acid, a phosphate such as sodium phosphate, potassium phosphate, acid pyrophosphate and polyphosphate, or a natural antioxidant such as α-tocopherol, rosemary extract, Vitamin C, green tea extract, glycyrhiza extract, chitosan, tannic acid and phytic acid.

A variety of additives, (e.g., amino acids, inorganic salts, vitamins, antibiotics, anti-bacterial substances, antioxidation, anti-fungal enzymes, living microorganisms, etc.) used as auxiliary component in the composition of the present invention is mixed with crops (e.g., homogenized or crushed wheat, oat, maize and rice), vegetable protein feed (e.g., one including rape, bean and sunflower as main ingredient), animal protein feed (e.g., blood meal, meat meal, bone meat and fish meat), sugar and milk products (e.g., dried component consisting of various milk powers and whey powder), and dry additive together; and then, may be utilized with substances such as nutrient supplement, digestion and absorption improver, growth stimulator and disease-preventive agent, besides main ingredient such as liquid component and liquid component generated by heating, i.e. lipid (e.g., plant oil, animal fat, etc.).

The composition of the present invention may be administrated to animals in combination with other feed additives of food carriers. The feed additive compositions of this invention may be feasibly administrated using various forms, for example, including top dressing, direct mixing with animal feed, or feed-independent oral formulations, or combination with other ingredients. Conventionally, the composition of the present invention may be used with amounts of a daily dosage or daily intake known to those of ordinary skill in the art.

According to still another preferred embodiment of this invention, the present composition may be provided as a pharmaceutical composition for treating a bacterial infection.

The pharmaceutical composition for treating a bacterial infection comprises (a) a therapeutically effective amount of an extract from a bark of *Alnus pendula*, or a compound represented by the formula I or II; and (b) a pharmaceutically acceptable carrier.

According to a preferred embodiment of this invention, the bacterial infection is an infection of *Staphylococcus aureus*.

The pharmaceutical composition of this invention includes a pharmaceutically acceptable carrier besides the active ingredient compounds, i.e. an extract from a bark of *Alnus pendula* or oregonin or hirsutenone.

The pharmaceutically acceptable carrier contained in the pharmaceutical composition of the present invention, which is commonly used in pharmaceutical formulations, but is not limited to, includes lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methylcellulose, methylhydroxy benzoate, propylhydroxy benzoate, talc, magnesium stearate, and mineral oils. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in *Remington's Pharmaceutical Sciences* (19th ed., 1995), which is incorporated herein by reference.

A suitable dosage amount of the pharmaceutical composition of the present invention may vary depending on pharmaceutical formulation methods, administration methods, the patient's age, body weight, sex, pathogenic state, diet, administration time, administration route, an excretion rate and sensitivity for a used pharmaceutical composition. Preferably, the pharmaceutical composition of the present invention may be administered with a daily dosage of 0.001-100 mg/kg (body weight).

The pharmaceutical composition according to the present invention may be administered orally or parenterally, and preferably, administered parenterally, e.g., by intravenous, subcutaneous, intramuscular, intra-abdominal or transdermal. It is desirable that the administration route of the present composition should be determined according to the disease to which the composition of this invention is applied.

The concentration of the extract from a bark of *Alnus pendula*, oregonin or hirsutenone of the present invention may be decided depending on treatment purpose, patient's conditions or administration period, and not limited to a concentration particularly.

According to the conventional techniques known to those skilled in the art, the pharmaceutical composition according to the present invention may be formulated with pharmaceutically acceptable carrier and/or vehicle as described above, finally providing several forms including a unit dose form and a multi-dose form. Non-limiting examples of the formulations include, but not limited to, a solution, a suspension or an emulsion in oil or aqueous medium, an elixir, a powder, a granule, a tablet and a capsule, and may further comprise a dispersion agent or a stabilizer.

The instant invention relates to a method of treating a bacterial infection in a subject in need of such treatment, which comprises administering to the subject an effective amount of an extract from a bark of *Alnus pendula*, or the compound represented by the following formula I or II.

The subject to whom the extract or compound of this invention is administered is preferably animal, more preferably mammal and most preferably human, but not limited to this.

According to a preferred embodiment of this invention, the bacterial infection is an infection of *Staphylococcus aureus*.

According to another preferred embodiment of the present invention, the extract from a bark of *Alnus pendula* is prepared by an extraction with a solvent selected from the group consisting of water, anhydrous or hydrated lower alcohol containing 1 to 4 carbon atoms, acetone, ethylacetate, butylacetate and 1,3-butylene glycol.

The technical features and merits of this invention are summarized as follows:

(i) The extract from a bark of *Alnus pendula*, compound represented by the following formula I or II of the present composition has an excellent anti-bacterial activity against bacteria, specifically *Staphylococcus aureus*.

(ii) The extract and compound of the present invention can be utilized as an active ingredient of drug, cosmetics, functional food and animal feed for treating a bacterial infection, specifically infection of *S. aureus*.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1

Isolation of Active Ingredients 1-1: Experimental Materials

Homogenized samples (300 g) dried on October, 2008 from Plant Extract Bank (Daejon, Korea) were utilized as the bark of *Alnus pendula* Matsum used in the present invention.

1-2. Instruments and Reagents

The instruments and reagents used in this invention are as follows:
a. $^1$H-NMR spectrometer: VNS 600 MHz (Varian, Palo Alto, USA)
b. $^{13}$C-NMR spectrometer: VNS 150 MHz (Varian, Palo Alto, USA)
c. GC-EI MS spectrometer: Autospec (Micromass, London, UK)
d. FAB MS spectrometer: JMS-600W Agilent 6890 Series (Jeol, Tokyo, Japan)
e. TLC: Adsorbent: Kieselgel 60 F254 (Merck, Darmstadt, Germany)
  Solvent (v/v): (a) $CHCl_3$: MeOH: $H_2O$=70:30:4
  Detection: (a) Ethanolic-$FeCl_3$ solution
    (b) 10%-$H_2SO_4$ in $H_2O$ (heating)
    (c) UV-lamp (254 nm)

f. Chromatographic gels:
  Sephadex LH 20, 75-230 μm mesh (Pharmacia, Uppsala, Sweden)
  MCI-gel CHP-20P, 75-150 μm (Mitsubishi, Tokyo, Japan)
g. Middle pressure liquid column chromatograph (MPLC):
  sample injector: Waters 650E (Waters, Milford Mass., USA)
  pump: TBP5002 (Tauto Biotech, Sanghai, China)
  detector: Gilson 112 UV/VIS 280 nm (Gilson Inc., Middleton, USA)
  gel: Daisogel (SP-120-40/60-ODS-B, Daiso Co., LTD., Osaka, Japan)
  data system: Autochro-Win 3.0 plus (Young-lin Co., Anyang, Korea)

1-3. Extraction and Isolation of Active Ingredients

Figure 1:
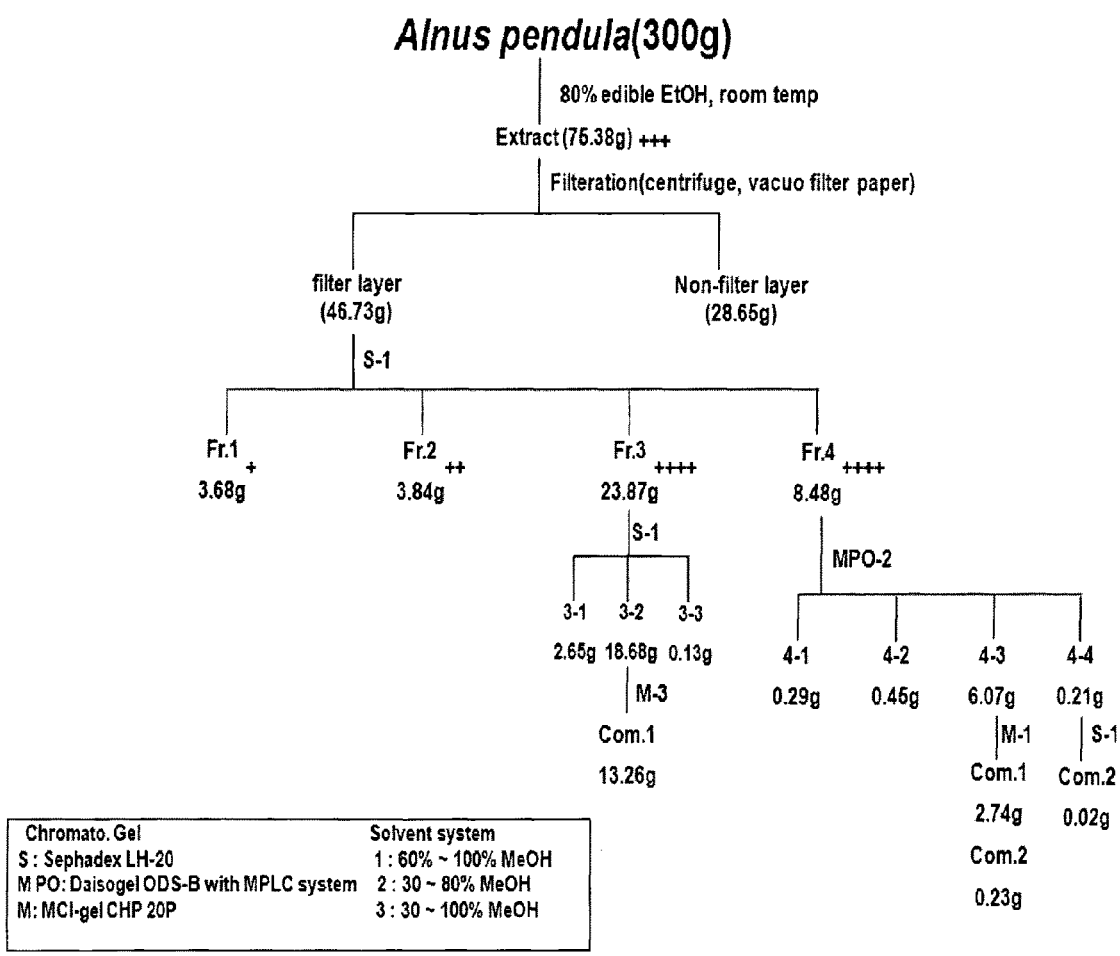
FIG. 1 schematically represents a process to isolate and purify an extract, fraction, and single compound having anti-bacterial activity from bark extracts of *Alnus pendula* Matum.

The fresh barks (300 g) of *Alnus pendula* Matsum were extracted three-times with 80% edible ethanol at room temperature. The extracted substances (75.38 g) were collected by concentrating the extract solutions under reduced pressure. The filter layer (46.73 g) and the non-filter layer (28.65 g) were obtained through filtration of the concentrated extracts. Subsequently, the filter layer was divided into four fractions (Fr 1, Fr 2, Fr 3, Fr 4) using Sephadex LH-20 column chromatography (80→400% MeOH, gradient system). The fraction-3 (Fr 3) having excellent anti-bacterial activity is further subjected to Sephadex LH-20 column chromatography (30→80% MeOH, gradient system), and divided into three sub-fractions (Fr 3-1, Fr 3-2, Fr 3-3). The sub-fraction Fr 3-2 was introduced into MCI-gel CHP 20P (30→100% MeOH, gradient system), yielding compound 1 (13.26 g). Fr-4 was divided into four fractions (Fr 4-1, Fr 4-2, Fr 4-3, Fr 4-4) with Daisogel ODS-B MPLC system (20→80% MeOH, gradient system). MCl-gel CHP 20P (80→400% MeOH, gradient system) of the fraction Fr 4-3 was carried out, obtaining compound 1 (2.74 g) and compound 2 (0.23 g). In addition, Sephadex LH-20 column chromatography (80→400% MeOH, gradient system) of the fraction Fr 4-4 was performed, yielding compound 2 (0.02 g) (FIG. 1).

1-4. TLC Test

Figure 2A:
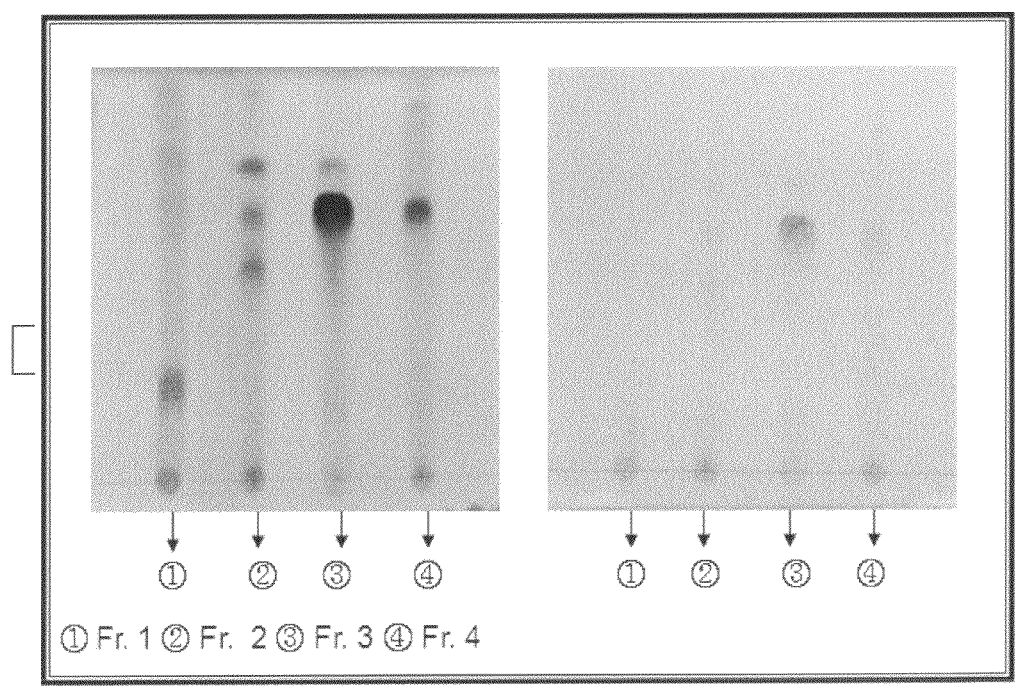
FIGS. 2a-2b represent TLC test for extracts and fractions of the present invention. TLC Plate: Silica gel, Solvent A: $CHCl_3$: MeOH: $H_2O$=70:30:4, Detection: $FeCl_3$ (I), 10% $H_2SO_4$ (II).
Figure 2B:
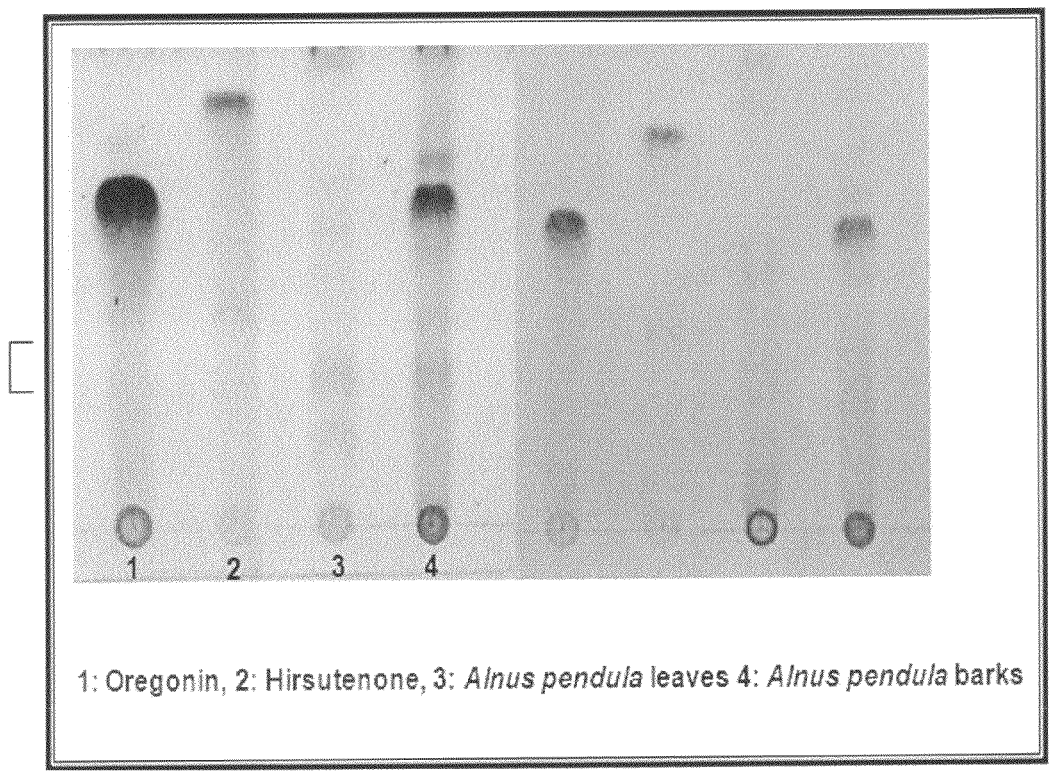

TLC analysis was carried out to analyze components of the bark of *Alnus pendula* Matsum. The bark of *Alnus pendula* Matsum was extracted with 80% edible ethanol. After filtration of the concentrated extracts, the filter layer and the non-filter layer were obtained. Using Sephadex LH-20 column chromatography with the solvent increased in a linear gradient from 80% to 100% methanol, the filter layer was divided into four sub-fractions (Fr 1, Fr 2, Fr 3, Fr 4), followed by TLC (Thin Layer Chromatography) test. $CHCl_3$/MeOH/$H_2O$=70/30/4 was used as a developing solvent, and next to developing, the colorimetric reaction was performed using a hot plate heating method after spraying iron chloride, anisaldehyde and 10% sulfuric acid. As results, it was shown that each fraction is effectively divided by TLC method, and oregonin and hirsutenone are putatively involved in the bark extract of *Alnus pendula* Matsum and fraction Fr 3 and Fr 4 thereof (FIGS. 2a-2b).

1-5. Structure of Compound 1 and 2

A. Compound 1

Compound 1 was a form of amorphous powder with brown color. In TLC test, compound 1 was detected as spots according to absorbance at UV lamp 254 nm wavelength. Compound 1 was positively represented by $FeCl_3$ spray, and detected as purple color by 10% $H_2SO_4$ spray and subsequently heating.

In $^1$H-NMR spectrum, the signal by one methylene, four methylene and methane having oxygen was represented in δ 1.76-1.80, δ 2.52-2.83 and δ 4.14, respectively. In aromatic moiety, the signal by two ABX-type was detected in δ 6.71-6.74 (4H in total, H-2',2",5',5") or 6.50-6.53 (2H in total, m, H-6",6'). In addition to, doublet signal (J=7.8 Hz) by anomeric hydrogen was shown in δ 4.31. Accordingly, compound 1 was postulated as glycoside of diarylheptanoid.

Additionally, two catechol rings were found in aromatic moiety of $^{13}$C-NMR spectrum. O-glycosylation was generated in one ketone (δ 210.6, C-3) and C-5 (δ 76.1) position of heptane moiety, inducing low magnetic field shift. Xylose (δ 104.0 74.6 77.5 70.8 66.6) was detected in sugar moiety, suggesting that compound 1 is 1.7-bis-(3,4-dihydroxy-phenyl)-heptane-3-on-5-O-β-D-xylopyranoside.

Furthermore, m/z 477 [M-H]$^-$ was determined using negative FAB MS spectrum (appendix FIG. 1-1). Finally, compound 1 was identified as (5S)-1,7-bis-(3,4-dihydroxyphenyl)-5-hydroxyheptane-3-on-5-O-β-D-xylopyranoside (oregonin) by comparison with data of references (25, 26).

brown amorphous powder
Negative FAB MS: m/z 477 [M-H]$^-$
$^1$H-NMR (600 MHz, DMSO-d$_6$+D$_2$O): δ 6.74-6.71 (4H in total, H-2',2",5',5"), 6.53-6.50 (2H in total, m, H-6",6'), 4.31 (1H, d, J=7.8 Hz, xyl-1), 4.14 (1H, m, H-5), 3.86 (1H, dd, J=11.4, 6.1 Hz xyl-5e), 3.54 (1H, m, xyl-4), 2.83-2.52 (8H in total, H-1,2,4,7), 1.80-1.76 (2H in total, m, H-6)
$^{13}$C-NMR (125 MHz, DMSO-d$_6$+D$_2$O, See the following Table 1)

B. Compound 2

Compound 2 was a form of amorphous powder with brown color. In TLC test, compound 2 was changed to dark green color by FeCl$_3$ spray, and detected as purple color by 10% H$_2$SO$_4$ spray and subsequently heating. In $^1$H-NMR spectrum, the signal by four methylene was represented in δ2.45-2.84, and doublet signal (J=16.0 Hz) by H-4 among hydrogen of alkene adjacent to C-3 ketone was detected in δ6.11. In aromatic moiety, the signal by a pair of ABX-types containing six hydrogen atoms was detected in 6.78-6.74 (4H in total, m, H-2',2",5',5"), 6.57-6.53 (2H in total, m, H-6',6"). Accordingly, it could be appreciated that compound 2 is a diarylheptanoid consisting of two catechol rings and one ketone, one ketone group and four methylene groups.

In addition, $^{13}$C-NMR spectrum represents two catechol rings and one ketone (δ210.3), carbon of alkene group (δ131.1, 147.5) and four methylene carbon atoms (δ29.9, 42.0, 34.8, 34.0), indicating that compound 2 has the structure of 1,7-bis-(3,4-dihydroxyphenyl)-4-heptene-3-one (Table 1 and appendix FIGS. 2-3). Additionally, M$^+$ peak at m/z 328 was observed in EI-MS spectrum (appendix FIG. 2-1). Consequently, compound 2 was isolated as hirsutenone by comparison with data of references (18, 21).

Brown oil
DIPEI MS: m/z 328.10 [M]
$^1$H-NMR (600 MHz, DMSO-d$_6$+D$_2$O): δ 6.92-6.85 (1H in total, m, H-5), 6.78-6.74 (4H in total, m, H-2',2",5',5"), 6.57-6.53 (2H in total, m, H-6',6"), 6.11 (1H, d, J=16.0 Hz, H-4), 2.84-2.45 (8H in total, m, H-1,2,6,7)
$^{13}$C-NMR (125 MHz, DMSO-d$_6$+D$_2$O, See the following Table 1)

TABLE 1

$^{13}$C-NMR data of compound 1 and 2

| Carbon number | 1* | 2* |
|---|---|---|
| Heptane moiety | | |
| C-1 | 29.7 | 29.9 |
| C-2 | 46.1 | 42.0 |
| C-3 | 210.6 | 210.3 |
| C-4 | 48.2 | 131.1 |
| C-5 | 76.1 | 147.5 |
| C-6 | 38.3 | 34.8 |
| C-7 | 31.4 | 34.0 |
| Diphenyl moiety | | |
| C-1' | 133.9 | 133.4 |
| C-1" | 134.9 | 133.7 |
| C-2' | 116.1 | 115.9 |
| C-2" | 116.2 | 116.0 |
| C-3' | 145.9 | 145.6 |
| C-3" | 145.9 | 145.6 |
| C-4' | 144.0 | 143.8 |
| C-4" | 144.3 | 143.9 |
| C-5' | 116.4 | 116.1 |
| C-5" | 116.5 | 116.1 |
| C-6' | 120.5 | 120.3 |
| C-6" | 120.4 | 120.2 |
| Sugar moiety | | |
| C-1 | 104.0 | |
| C-2 | 74.6 | |
| C-3 | 77.5 | |
| C-4 | 70.8 | |
| C-5 | 66.6 | |
| C-6 | (xyl) | |

*125 MHz (DMSO-d$_6$ + D$_2$O)

C. Chemical Structure of Compound 1 and 2

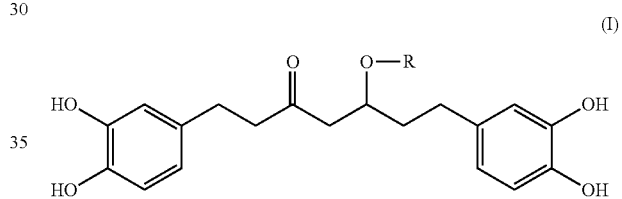

(I)

wherein R represents xylose in formula I.
[(5S)-1,7-bis-(3,4-dihydroxyphenyl)-5-hydroxyheptane-3-on-5-O-β-D-xylopyranoside]

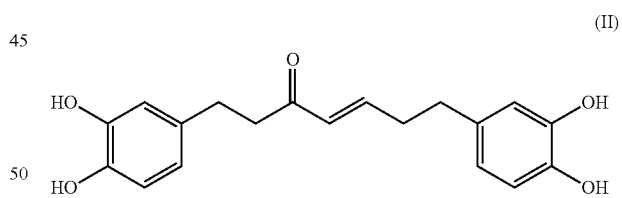

(II)

1,7-bis-(3,4-dihydroxyphenyl)-4-heptene-3-one

Example 2

Anti-Oxidative Activity Analysis 2-1: Measurement of Scavenging Activity to Free Radical Using DPPH According to Hatano's method (80), each *A. pendula* extract and sample of the fraction Fr 1, Fr 2, Fr 3 or Fr 4 was prepared at six final concentrations of 3.125 μg/ml, 6.25 μg/ml, 12.5 μg/ml, 25 μg/ml, 50 μg/ml and 100 μg/ml. Meanwhile, each compound 1 and 2, obtained from the fraction Fr 3 and Fr 4 of *A. pendula* extract, was prepared at six final concentrations of 3.125 μM/ml, 6.25 μM/ml, 12.5 μM/ml, 25

μM/ml, 50 μM/ml and 100 μM/ml. Each sample (10 μL) was incubated with 0.1 mM DPPH solution (180 μL, in 99.5% ethanol), and vigorously agitated for 10 sec using a vortex mixer, followed by incubation for 30 min at 37° C. Afterwards, the absorbance was measured at 492 nm using an ELISA reader (TECAN, Sazburg, Austria).

L-ascorbic acid as positive control drug was prepared and measured according to the method as described above. To determine anti-oxidative activity of each sample, anti-oxidative potential was represented as reducing power by EDA % (Electron donating ability) for DPPH. Additionally, $IC_{50}$, defined as the amount of sample in which EDA is responsible for 50%, was measured to assess anti-oxidative activity of samples, respectively.

2-2: Results of Anti-Oxidative Activity Analysis

DPPH method is a representative measuring anti-oxidative activity (81). DPPH contains stable radical in normal condition, but its radical was removed where it contacts with a substance having anti-oxidative activity. Therefore, anti-oxidative effects could be assessed by measuring the absorbance changes of DPPH. In this regard, DPPH as a relatively stable free radical in dark-purple state was reduced by amino acids containing sulfur atom such as cystin and glutathione, L-ascorbic acid, BHA or BHT. These color changes have been used to isolate an anti-oxidative substance from a variety of natural materials (82).

Where the extract from a bark of *A. Pendula* and the fraction Fr 1, Fr 2, Fr 3 or Fr 4 thereof isolated by Sephadex LH-20 column chromatography were used in measurement of scavenging activity to free radicals, *A. Pendula* extracts ($IC_{50}$=16.36±1.26 μg/ml) represented inhibitory activities for free radical less than positive control, L-ascorbic acid ($IC_{50}$=5.29 ±0.05 μg/ml), and the fractions isolated by column chromatography showed inhibitory activities for free radicals in a sequence of Fr 4>Fr 3>Fr 2>Fr 1. In particular, the fraction Fr 4 ($IC_{50}$=9.41±0.41 μg/ml) represented much more excellent scavenging activity for free radicals compared with positive control, L-ascorbic acid ($IC_{50}$=5.29 ±0.05 μg/ml). As described above, DPPH method was carried out for compound 1 (oregonin) and compound 2 (hirsutenone) isolated from Fr 3 and Fr 4 with prominent scavenging activity for free radicals. As results, compound 1 ($IC_{50}$=15.59±0.35 μg/ml) and compound 2 ($IC_{50}$=22.53±0.71 μg/ml) had much more remarkable scavenging activity for free radicals compared with the positive control, L-ascorbic acid ($IC_{50}$=5.29±0.05 μg/ml). Interestingly, the compound 1 represented anti-oxidative activity much higher than the positive control.

TABLE 2

$IC_{50}$ value of extracts and fractions of the present invention in DPPH radical scavenging activity

| Fraction | DPPH radical scavenging activity (μg/ml) |
|---|---|
| extract | 16.36 ± 1.26 |
| Fr. 1 | 55.67 ± 2.76 |
| Fr. 2 | 21.78 ± 1.04 |
| Fr. 3 | 10.23 ± 0.28 |
| Fr. 4 | 9.41 ± 0.41 |
| Vit. C | 5.29 ± 0.05 |

TABLE 3

$IC_{50}$ value of compounds of the present invention in DPPH radical scavenging activity

| Compound | DPPH radical scavenging activity (μM) |
|---|---|
| compound 1 (oregonin) | 15.59 ± 0.35 |
| compound 2 (hirsutenone) | 22.53 ± 0.71 |
| Vit. C | 16.37 ± 0.21 |

Example 3

Anti-Bacterial Activity Analysis 3-1. Strains and Cell Culture

A. Strains

*S. aureus* MSSA ATCC 25923 and MRSA 33591 standard strains were purchased from Korean Culture Center of Microorganisms (KCCM), and two *S. aureus* clinical isolates were obtained from subjects of WonKwang University Hospital (Iksan, Jeonbuk, South Korea). Mueller Hinton Agar (MHA, Difco, USA) or Mueller Hinton Broth (MHB, Difco, USA) was used as subculture media.

B. Cell Culture

All media and instrument used was sterilized using autoclave (for 15 min at 121° C. under 1.3 atmospheric pressure), and strains were stored at −70° C.

3-2. Measurement of Anti-Bacterial Activity Using Liquid Media Dilution Assay

Minimum Inhibitory Concentration (MIC) was carried out according to the standard of Clinical and Laboratory Standards Institute (CLSI). One strain of MRSA (Methicillin resistant *staphylococcus aureus*), one strain of MSSA (Methicillin susceptible *staphylococcus aureus*, MSSA), and two strains of MRSAs as clinical isolates obtained from plastic surgery subjects of WonKwang University Hospital, were suspended in Muller-Hinton Broth. Thereafter, the bacterial solutions were adjusted to the turbidity of 0.5 Mcfarland standard. The bacteria were prepared at a concentration of about 1×10$^8$ CFU/ml, followed by performing anti-bacterial experiment using a liquid media dilution assay.

The extract from a bark of *Alnus pendula* was serially diluted from minimal concentration (0.97 μg/ml) to maximal concentration (2 mg/ml) using DMSO (Dimethylsulfoxide) as a solvent, and then were seeded into each well of 96-well plate with a volume of 10 μl/well, followed by adding 100 μl bacterial solution and 90 μl media. After culturing the mixture for 24 hrs at 37° C. in incubator, MIC was defined as minimal concentration in which the growth of bacteria is inhibited in a naked-eye observation. Ampicillin was serially diluted from minimal concentration (0.06 μg/ml) to maximal concentration (250 μg/ml), and incubated under culture conditions of the bark extract of *Alnus pendula* as described above. It was verified that the solvent and DMSO used have no any effect on anti-bacterial activity of each sample.

3-3. Results of Anti-Bacterial Activity Analysis

To examine anti-bacterial activity of the bark extract of *Alnus pendula*, MIC of samples was measured using a liquid media dilution assay. As results, MICs of the extract from a bark of *Alnus pendula* against *S. aureus* MSSA ATCC 25923, MRSA 33591, DPS-1 and 2 strains were measured in a range of 125-250 μg/ml, demonstrating that the extract from a bark of *Alnus pendula* has much more superior anti-bacterial activity than positive control, ampicillin (0.12-125 μg/ml). In addition, MICs of the fractions of *Alnus pendula* extract against *S.* aureus MSSA ATCC 25923, MRSA 33591, DPS-1 and 2 strains were measured in a range of 125-2000 µg/ml, indicating excellent anti-bacterial activity of the fractions used in the present invention (See, the following Table 4).

TABLE 4

MIC (minimum inhibitory concentration) of edible ethanol extract of the *Alnus pendula* bark (AP) and ampicillin (AMP) against various *S. aureus* strains.
Anti-bacterial activity (extract)

| | MIC (µg/ml) | |
|---|---|---|
| Strains | AP | AMP |
| *S. aureus* ATCC 25923 (MSSA) | 125 | 0.12 |
| *S. aureus* ATCC 33591 (MRSA) | 250 | 125 |
| *DPS-1 (MRSA) | 250 | 125 |
| *DPS-2 (MRSA) | 250 | 125 |

*DPS indicates *S. aureus* strains provided from Department of Plastic Surgery of WonKwang University Hospital.

In particular, anti-bacterial activity was higher in a sequence of Fr 4>Fr 3>Fr 2>Fr 1, because either compound 1 (oregonin) or compound 2 (hirsutenone) were contained in the fraction Fr 3 or Fr 4 (See, the following Table 5).

TABLE 5

MIC (minimum inhibitory concentration) of fraction-1 (Fr-1), fraction-2 (Fr-2), fraction-3 (Fr-3) and fraction-4 (Fr-4) of edible ethanol extracts of the *Alnus pendula* bark and ampicillin (AMP) against various *S. aureus* strains.
Anti-bacterial activity (sub-fraction)

| | MIC (µg/ml) | | | | |
|---|---|---|---|---|---|
| Strains | Fr-1 | Fr-2 | Fr-3 | Fr-4 | AMP |
| *S. aureus* ATCC 25923 (MSSA) | 2000 | 500 | 250 | 125 | 0.12 |
| *S. aureus* ATCC 33591 (MRSA) | 2000 | 500 | 250 | 125 | 125 |
| *DPS-1 (MRSA) | >2000 | 500 | 250 | 250 | 125 |
| *DPS-2 (MRSA) | >2000 | 500 | 250 | 250 | 125 |

*DPS indicates *S. aureus* strains provided from Department of Plastic Surgery of WonKwang University Hospital.

As described above, anti-bacterial activity of each compound 1 (oregonin) and compound 2 (hirsutenone) isolated from the fraction Fr 3 and Fr 4 against *S. aureus* MSSA ATCC 25923, MRSA 33591, DPS-1 and 2 strains, was measured in a range of 62.5-250 µg/ml, suggesting noticeable anti-bacterial activity of the compounds used in the present invention. In contrast with results of anti-oxidative activity analysis, the anti-bacterial activity of compound 2 (hirsutenone) was adjacent to anti-bacterial activity of ampicillin compared with that of compound 1 (oregonin). Consequently, it was demonstrated that Fr. 4 containing both compound 1 and 2 represented much more remarkably great anti-bacterial activity (See, the following Table 6).

TABLE 6

MIC (minimum inhibitory concentration) of fraction-4 (AP-4) of edible ethanol extracts of the *Alnus pendula* bark, oregonin (compound 1, ORE), hirsutenone (compound 2, HIR), and ampicillin (AMP) against various *S. aureus* strains.
Anti-bacterial activity (compound)

| | MIC (µg/ml) | | | |
|---|---|---|---|---|
| Strains | AP4 | ORE | HIR | AMP |
| *S. aureus* ATCC 25923 (MSSA) | 125 | 250 | 62.5 | 0.12 |
| *S. aureus* ATCC 33591 (MRSA) | 125 | 250 | 62.5 | 125 |

TABLE 6-continued

MIC (minimum inhibitory concentration) of fraction-4 (AP-4) of edible ethanol extracts of the *Alnus pendula* bark, oregonin (compound 1, ORE), hirsutenone (compound 2, HIR), and ampicillin (AMP) against various *S. aureus* strains.
Anti-bacterial activity (compound)

| | MIC (µg/ml) | | | |
|---|---|---|---|---|
| Strains | AP4 | ORE | HIR | AMP |
| *DPS-1 (MRSA) | 250 | 250 | 125 | 125 |
| *DPS-2 (MRSA) | 250 | 250 | 62.5 | 125 |

*DPS indicates *S. aureus* strains provided from Department of Plastic Surgery of WonKwang University Hospital.

Having described a preferred embodiment of the present invention, it is to be understood that variants and modifications thereof falling within the spirit of the invention may become apparent to those skilled in this art, and the scope of this invention is to be determined by appended claims and their equivalents.

REFERENCES

1. Lee. Y. N., Coloured Resources Plants of Korea, Kyohak Co., (1997)
2. Korea Plants Anatomy. Academy Book, Seoul, (1996)
3. Asakawa, Y., Genjida, F., Mayashi, S. and Matsuura, T.: A Nea ketol from *Alnus firma* (Betulaceae). Tetrahedron Letters, 3235-3237 (1969)
4. Asakawa, Y.: chemical constituents of *Alnus siebodiana*. III. The systhesis and stereochemistry of yashabushiketols. Bull. Chem . . . Soc, 45, 1494-1797 (1972)
5. Suga, T., Iwata, N. and Asakaw, Y.: Chemical constisuents of male flower of *Alnus pendula*. Bull. Chem. Soc. Jap., 45,2058-2060 (1972)
6. Karches, J. J. and Laever. A. M. L.: Struture of oregonin, a natural diarylhheptanoid xyloside. J. C. S. chem., 649-650 (1974)
7. Nomura, M., Tokoroyama, T. and Kubota, T.: Three new cyclized C9-C1-C9 compounds from *Alnus japonica* Steud, J. C. S. Chem, 65-66 (1974)
8. Nomura, M., Tokoroyama, T. and Kubota, T.: Further phenolic components from *Alnus japonica* steud. J. C. S. Chem. Comm, 316-317 (1975)
9. Nomura, M., Tokoroyama, T. and Kubota, T.: diarylheptanoids and other constituents from wood of *Alnus japonica* Phytochemistry, 20, 1097-1104 (1981)
10. Suga, T., Ohta, S., Hirata, T. and Aoki, T.: The absolute configuration of diarylheptanoid xyloside, oregonim, isolated from the female flowers of *Alnus serrulatoides*. Chem. Lett., 895-898 (1982)
11. Suga, T., Ohta, S., Hirata, T. and Aoki, T.: An X-ray crystallographic study on the absolute configuration of dihydroyashabushiketol and the solvent-depence of its optical rotation Bull. Chem. Soc. Jpn, 56, 3353-3357 (1983)
12. Terazawa, M., Okuyama, H., Miyake. M. and Sasaki. M.: Phenolic compounds in living tissue of wood IV: Hirsutoside from the green bark of keyamahannoki (*Alnus hirsta*) [Betulaceae] and its seasonal variation in the living tissues of hannoki(A japonica)., Mokuzai Ciakonishi, 30, 587-600 (1984)
13. Ohta, S., Aoki, T., Hirata, T. and Suga, T.: The structures of four diarylheptanoid glycosides from the female flowers of *Alnus serrulatoides*, J. Chem. Soc. Perkin. Trans. I, 8, 1635-1642 (1984)

14. Sasaya, T.: Diarylheptanoids of *Alnus hirsuta* Turcz (Betulaceae). Enshurin Kenkyu Hokoku (Hokkaido Daigaku Nogakubu), 42, 191-205 (1985)
15. Hashimoto, T., Tori, M. and Asakawa, Y.: Five new diarylheptanoids from the male flowers of *Alnus siebodiana*. Chem. Pharm. Bull., 34, 1846-1849 (1986)
16. Aoki, T., Ohta, S. and Suga, T.: Triterpenoids, diarylheptanoids and their glycosides in the flowers of *Alnus* species, Phytochemistry, 23, 3611-3624 (1990)
17. Lee, M. W., Tanaka, T, Nonaka, G. and Nishioka, I.: Hirsunin, an ellagitannin with a diarylheptanoid moiety from *Alnus hitsuta* var. micropaylla, Phytochemistry, 31, 967-970 (1992)
18. Tori, M., Hashimoto, A., Hirose, K. and Asakawa, Y.: Diarylheptanoids, flavonoids, stilbenoids, sesquiterpenoids and a phenanthrene from *Alnus maximowiczii*. Phytochemistry, 40, 1263-1264 (1965)
19. Bae, C. I., Gong, J. M., Oh, J. W., Kim, H. J., Oh, G. J., Park, S. K., Chung, S. G. and Cho, E. H.: Studies on the cytotoxic constituent of *Alnus hirsute* (Spach) RupR. Yakhak Hoeji, 41, 559-564 (1997)
20. Chen, J., Karchesy, J. J. and Gonzalez-Laredo, R. F.: Phenolic diaryiheptenone from *Alnus rebura* bark. Planta Med. 64, 74-75 (1998)
21. Gonzales-laredo, R. F., Helm, R. F., Chen, J. and Karchesy, J. J.: Two acylated diarylheptanoid glycosides from red alder bark. J. Nat. Prod., 61, 1292-1294 (1998)
22. Wada, H. Tachibana, H., Fuchino, H. and Tanaka, N.: Three new diarylheptanoid glycosides from *Alnus japonica*, Chem. Pharm. Bull., 46, 1054-1055 (1998)
23. Gonzalez-Laredo, R. F., Chen, J., Karchesy, Y. M. and Karchesy, J. J.: Four new diarylheptanoid glycosides from *Alnus rubra* bark, Natural Products Letters, 13, 75-80 (1990)
24. Lee, M. W., Park, M. S., Jeong, D. W., Kim, K. H., Kim, H. H. and Toh, S. H.: Diarylheptanoids from the leaves of *Alnus hirsute* Turcz, Arch. Pharm. Res., 23, 50-53 (2000)
25. Jeong, D.-W., kim, J.-S., Cho, S.-M., Lee, Y.-A., Kim, K.-H., Kim, S.-W. and Lee. M.-W.: Diarylheptanoids from the barks of *Alnus hirsute* var. Sibirica, Kor. J. Phamacog., 31, 28-33 (2000)
26. Suga, T., Iwata, N. and Asakawa, Y.: Chemical constituents of the male flower of *Alnus pendula* (Betulaceae), Bull. Chem. Soc. Jpn., 45, 2058-2067 (1972)
27. Lim, H-W., Kim, M-K., Kim, H-J., Shim, J-G., Kim, G-H., Choi, H-K., Lee, M-W.,: Quantitative Determination of Diarylheptanoid Compounds from Korean *Alnus*, Kor. J. Pharmacogn. 35(4): 384~387 (2004)
28. Asakawa, Y.: Chemical constituents of *Alnus sieboldiana* (Betulaceae) II. The isolation and structure of flavonoids and stilbenes. Bull. Chem. Soc. Jph., 44, 2761-2766 (1971)
29. Stikhin, V, A., Ban'kovskii, A, I., Glyzin, V, I. and Kir'yanova, I, A.: Quercetin-3-sophoroside from *Alnus glutinosa* and *Fraxinus Lanceolata* pollens. Chem . . . Nat. Comp., 10, 526 (1974)
30. Lee, M.-W., Jeong, D.-W., Lee. Y.-A., Park, M.-S., Jeong, D.-W. and Toh, S.-H.: Flavonoids from the leaves of *Alnus hirsute*, Yakhak Hoeji, 43, 547-557 (1999)
31. Ahn, K.-W., Toh, S.-H., Jeong, D.-W., Kim J.-S., Cho, maximowiczii Call, Yakhak Hoeji, 44, 41-46 (2000)
32. karchesy, J. J., Loveland, P. M., Laver, M. L., Barofsky, D. *Alnus rubra* and *Pseudotsuga menziesii*. Phytochemistry, 15, 2009-2010 (1976)
33. Yu, Y-B., Norio Nakamura., Hirotsugu Miyashiro, Masao Hattori, Park, J-.: Triterpenoid and Flavonoid compounds of *Alnus* leaves, 76-83 (2007)
34. Yu, Y-B., Norio Nakamura., Hirotsugu Miyashiro, Masao Hattori, Park, J-.: Effects of Triterpenoids and Flavonoids Isolated from *Alnus firma* on Hiv-1 Viral Enzymes, No 7, 820-826, (2007)
35. Karchesy, J, J., Loveland, P, M., Laver, M, L., Barofsky, D, F. and Barofsky, E.: Condensed tannins from the barks of *Alnus rubra* and *Pseudotsuga menziesii*. Phytochemistry, 15, 2009-2010 (1976)
36. Yoshida, A. T, Memon, M. U. and Okuda, T.: Alnusin, A novel ellagitannin from *Alnus sieboldiana* fruits. Heterocycles, 16, 1085-1088 (1981)
37. Ishimatsu, M., Tanaka, T., Nonaka, G. and Nishioka, I.: Alnusnin A and B from the leaves of *Alnus siebodiana*. Phytochemistry, 28, 3179-3184 (1989)
38. Khvorst, O. P., Serbin, A. G., Komissarenko, N. F. and Goldienko, V. G.: Ellagitannins derived from *Alnus glutinosa*(L). Khim Farm Zh, 23, 445-449 (1989)
39. Lee, M. W., Tanaka, T., Nonaka, G. I. and Nishioka, I.: Dimeric ellagitannins from *Alnus japonica*. Phytochemistry, 31, 2835-2839 (1992)
40. Hirata, T., Murai, K., Ideo, R. and Suga, T.: Triterpenoids in the male flower of *Alnus serrulatoides*. prosymp. Chem. Nat. Prod., 273 (1976).
41. Hirata, T. and Suga, T.: Crystal and molecular structure of alnuserol, a new 11-hydroxylated C13 dammarane-type triterpene from *Alnus serrulatoides*, J. Chem Soc. Perkin. Trans., 347 (1978)
42. Suga, T., Aoki, T., Hirata, T., Aoki, K. and Asakawa, Y.: Structure of alnustic acid a new secodammarane type triterpeneic acid from *Alnus sieboldiana*, Bull, Chem. Soc. Jpn., 52, 1698-1700 (1979)
43. Suga, T. and Hirata, T.: New C-31 secidamarane-type triterpenoids, alnuseric acid and alnuselide, in the male flowers of *Alnus serrulatoides*, Dept. Chem. Soc. Jpn., 52, 1153 (1979)
44. Xuj, D., Wei, C, C. and Sung, C, C.: Chemical study triterpene compounds in *Alnus tinctoria* sarg. Isolation and identification of lupenone. Pai Ch'iu en I K'o to Hseuh Hseuh pao, 6, 4-8 (1980)
45. Aoki, T., Ohta, S., Aratani, S., Hirata, T. and Suga, T.: The structure of four novel C13-secodammarane-type triterpenoid saponins from the female flowers of *Alnus serrulatoides*. J. Chem. Soc. Perkin. Trans. I, 1399-1403 (1982)
46. Hirata, T., Ideo, R., Aoki, T. and Suga, T.: The structure of alnuserrutriol, a new C31 dammarane-type triterpenoid from the male flowers of *Alnus serrulatoides*. Bull. Chem. Soc. Jpn., 55, 640 (1982)
47. Talapatra, S. K., Chattopadhyaya, P. and Talapatra, B.: Triterpenoid and related compounds. Part XXXIII. Triterpenoid constituents of *Alnus nepalensis* D. Don. J. Indian Chem. Soc., 60, 203 (1983)
48. Suga, T., Aoki, T., Kawada, Y., Ohta, S. and Ohta, E.: C-secodammarane-type triterpenoid saponins from the male flowers of *Alnus pendula*. Phytochemistry, 23, 1297-1299 (1984)
49. Ohta, S., Aoki, T., Hirata. And Suga, T.: The structures of four diarylheptanoid glycosides from the female flowers of *Alnus serrulatorides*, J. Chem. Soc. PerkinTrans. I, 1635-1642 (1984)
50. Sakamura, F., Ohta, S., Aoki, T. and Syga, T.: Triterpenoids from the female and male flowers of *Alnus sieboldiana*, Phytochemistry, 24, 2744-2745 (1985).
51. Suga, T., Ohta, S., Ohta, E. and Aoki, T.: A C-31-secodammarane-type triterpenic acid, 12-deoxy alnustic acid from the female flowers of *Alnus pendula*. Phytochemistry, 25, 1243-1244 (1986)

52. Lee, J.-H., Yeom, S.-H., Kim, H.-J., Shim, J.-G., Lee, M-W.,: Anti-oxidative Activities of Dirylheptanoids from *Alnus japonica* and Their Structural Relationship, Kor. J. Pharmacogn.34(2): 190-192 (2003)
53. Kim, H.-J., Yeom, S.-H., Kim, M-K., Shim, J-G., Paek, I-N., Lee, M-W.,: Nitric Oxide and Prostaglandin E2 Synthasis inhibitory Activities of Diarylheptanoids from the Barks of *Alnus japonica* Steudal. No 2, 177-179, (2005)
54. Choi, S-E., Kim, K-H., Kwon, 3-H., Kim, S-B., Kim, H-W., Lee, M-W.,: Cytotoxic Activies of Diarylheptanoids from *Alnus japonica*, N0 10, 1287-1289, (2008)
55. Sin, S, J. and Ahn, W, Y.: Some Triterpenoids in Bark of Korean Water Alder, *Alnus Hirsuta* Ruprecht. Forestry Energy, 11, 36-44 (1991)
56. Sheth, K., Bianchi, E., Wiedhopf, R. and Cole, 3, R.: Antitumor agents from *Alnus oregona* (Betulaceae). J. Pharm. Sci., 62, 139 (1973)
57. Kawai, N., Ando, Y. U., Ando, Y. O. and Nishibe, Y.: Extraction of antimutagenic tannins from *Alnus firma* plant, Patent-Japan Kokai Tokyo Koho-O2 117, 685 (1990)
58. Saxena, G., Farmer, S., Hancock, R. E. W. and Towers, G. H. N.: Antimicrobial compounds from *Alnus rubra*. Int. J. Pharmacogn., 33, 33-36 (1995)
59. Lee, D. I., Chang, J. K., Lee, M. W. and Hong, S. G.: Effects of oregonin, diarylheptanoid derivative from plant on antitumor, Chung-Ang J. Pharm. Sci., 12, 67-72 (1998)
60. Lee, M. W., Kim, N. Y., Park, M. S., Ahn, K. H., Toh, S. H., Hahn, D. R., Kim, Y. C. and Chung, H. T.: Diarylheptanoids with in vitro inducible nitric oxide synthesis inhibitory activity from *Alnus hirsute*, Planta, Med., 66, 551-553 (2000)
61. Lee, M. W., Kim, J. H., Jeong, D. W., Ahn, K. H., Toh, S. H. and Surh, Y. J.: Cyclooxygenase-2 inhibitory effect of diarylheptanoids from the barks of *Alnus hirsute* var. sibirica, Bio. Pharm. Bull., 23, 517-518 (2000)
62. Lee, Y. A., Jeong, D. W., Kim, K. H., Kim, J. S., Kim, S. W. and Lee, M. W.: Antioxidant activity of diarylheptanoids from the leaves of *Alnus hirsuta*, Yakhak Hoeji, 47, 193-196 (2000)
63. Choi, E-J., Ko, H-H., Lee, C-S., Bang, H., Lee, M.-W.,: Inhibition of activated responses in dendritic cells exposed to lipopolysaccharide and lipoteichoic acid by diarylheptanoid oregonin, 8, 748-755, (2008)
64. Michael J C. The role of *Staphylococcs aureus* in atopic eczema: treatment strategies. J Eur Acad Dermatol Venereol, 7(1 Suppl): 31S7S (1996)
65. Bibel D J, Aly R, Shinefield H R, Maibach J H, Strauss W G. Importance of the keratinized epithlial cell in bacterial adherence. J Invest Dermatol; 79, 250-3 (1982)
66. Park S. N.: Anti-oxidative properties of baicalein, component from *Scutellaria baicalensis* georgl and its application to cosmetic (I), J. Korean Ind Eng Chem, 14(5): 657-665 (2003)
67. Sugifra H, Umemoto N, Duguchi H, Murata Y, TanaKa K, Sawai T, et al. Prevalence of chilhood and adolescent stopic dermatitis in a Japanese population; comparison with the disease frequency examined 20 years ago. Acta Derm Venereol; 78: 293-4 (1998)
68. Lee S K, Chang D S. Positive functions of reactive oxygen species. Science & Technology file. 28-29 (2006)
69. Shin Y J. Antioxidant and Anti-imflammatory effects of fractions from Dandeliom (*Taraxacum officinale*) leaf and root. Seoul University Articles. (2006)
70. cole G W, Silverberg N L. The adherence of *Staphlococcus aureus* to human corneocytes. Arch Dermatol ; 122, 166-9, (1986)
71. Ohnishi Y, Okino N, Ito M, Orryama S. Ceramidase activity in bacterial skin flora as a possible cause of ceramide deficiency in atopic dermatitis. clin Diagn Lab Immunol; 6, 101-4, (1999)
72. Leung D Y, Tharp M, Atopic dermatitis. in:Freeberg I M, Eisen A Z, Wolff K, Austen K F, Goldsmith L A, Katz S I, et al. editors. Dermatology in general medicine. 5th ed. New York: McGraw-Hill, :1464-80, (1999)
73. Leung D Y. Atopic dermatitis and the immune system: the role of superantigens and bacteria. J Am Acad Dermatol; 45, 1 Suppl: 13S-6S, (2001)
74. Leung D Y. Cellular and immunologic mechanism in atopic dermatitis. J Am Acad Dermatol;44(1 Suppl), 1S-12S, (2001)
75. Laver R, Hadley K, Downey D, Mackie R. Staphylococcal colonization in atopic dermatitis and the effect of topical mupirocin therapy. Br J Dermatol;119, 189-98, (1988)
76. Nilsson E J, Hennings C G, Magnusson J. Topical coeticosteroids and *staphylococcus aureus* in atopic dermatitis. J Am Acad Dermatol; 27, 29-34, (1992)
77. Leung D Y M. Role of *staphylococcus aureus* in atopic dermatitis. in Leung F Y M, Bieber T(ed). p 401-18, Marcel Dekler INC., New York, (2002)
78. Hisanori A, Osamu Y, Joji T, Jiro A. Adherence characterisitics and susceptibility to antimicrobial agents of *Staphylococcus aureus* strains isolated from skin infections and atopic dermatitis. J of Dermatol Sci;23, 155-60, (2000)
79. Nishijima S, Kurokawa I, Nakaya H. Susceptibility change to antibiotics of *Staphylococcus aureus* strains isolated from skin infections between July 1994 and November 2000. J Infect chemother;8, 187-9, (2002)
80. Hatano, T., Edamatsu, R., Hiramatsu, M., Mori, A., Fujita, Y., Yasuhara, T., Yoshida, T. and Okuda, T.,: Effects of the interaction of tannins with co-exist substances. IV Effects of tannins and related polyphenols on superoxide anion radical, and on 1,1-diphenyl-2-picryihydrazyl radical. Chem. Pharm. Bull., 37, 2016 (1989)
81. Bbis, M. S. Antioxident determination by the use of a stable free radical. Nature. 26: 1199-1120, (1958)
82. Kim, J. H. and Park, K. M. Nitrite scaverging and superoxide dismutaselike activities of herbs, spices and curry. Korean J. Food Sci. Technol. 32: 706-712, (2000)

What is claimed is:

1. A method of treating Methicillin resistant *Staphylococcus aureas* infection in a subject infected with Methicillin resistant *Staphylococcus aureas* comprising administering to said subject a therapeutically effective amount of an isolated fraction from an ethanol extract of *Alnus pendula* bark, wherein the isolated fraction contains therapeutically effective amounts of oregonin and hirsutenone and is obtained by filtration.

* * * * *